(12) United States Patent
Maskin

(10) Patent No.: US 8,906,427 B2
(45) Date of Patent: Dec. 9, 2014

(54) TREATMENT FOR MEIBOMIAN GLAND DYSFUNCTION OR OBSTRUCTION

(71) Applicant: MELBJ Holdings, LLC, Tampa, FL (US)

(72) Inventor: Steven Maskin, Tampa, FL (US)

(73) Assignee: MELBJ Holdings, LLC, Tampa, FL (US)

( * ) Notice: Subject to any disclaimer, the term of this patent is extended or adjusted under 35 U.S.C. 154(b) by 140 days.

(21) Appl. No.: 13/743,600

(22) Filed: Jan. 17, 2013

(65) Prior Publication Data

US 2013/0131171 A1    May 23, 2013

Related U.S. Application Data

(60) Division of application No. 12/780,730, filed on May 14, 2010, which is a continuation-in-part of application No. 11/069,239, filed on Mar. 1, 2005, now abandoned.

(60) Provisional application No. 60/562,683, filed on Apr. 15, 2004, provisional application No. 60/552,577, filed on Mar. 12, 2004.

(51) Int. Cl.
| | | |
|---|---|---|
| *A61K 36/00* | (2006.01) | |
| *A61K 31/23* | (2006.01) | |
| *A61K 45/06* | (2006.01) | |
| *A61K 31/167* | (2006.01) | |
| *A61K 36/185* | (2006.01) | |
| *A61K 31/231* | (2006.01) | |
| *A61K 31/215* | (2006.01) | |

(52) U.S. Cl.
CPC ............... *A61K 31/231* (2013.01); *A61K 31/23* (2013.01); *A61K 45/06* (2013.01); *A61K 31/167* (2013.01); *A61K 36/185* (2013.01); *A61K 31/215* (2013.01)
USPC ........................................................ 424/725

(58) Field of Classification Search
None
See application file for complete search history.

(56) References Cited

U.S. PATENT DOCUMENTS

| | | | |
|---|---|---|---|
| 4,585,656 | A | 4/1986 | Rosenthal |
| 4,588,717 | A | 5/1986 | Mitchell |
| 4,866,049 | A | 9/1989 | Maumenee |
| 4,914,088 | A | 4/1990 | Glonek |
| 5,188,826 | A | 2/1993 | Chandrasekaran |
| 5,371,108 | A | 12/1994 | Korb |
| 5,604,200 | A | 2/1997 | Taylor-McCord |
| 5,696,166 | A | 12/1997 | Yanni |
| 5,968,500 | A | 10/1999 | Robinson |
| 6,043,213 | A | 3/2000 | Tsubota |
| 6,156,703 | A | 12/2000 | Hicks |
| 6,464,990 | B2 | 10/2002 | Simonnet |
| 6,559,182 | B1 | 5/2003 | Purcell |
| 6,846,499 | B2 | 1/2005 | Mogy |
| 2003/0008022 | A1 | 1/2003 | Mogy |

FOREIGN PATENT DOCUMENTS

| | | |
|---|---|---|
| EP | 0535545 | 4/1993 |
| EP | 0875244 | 11/1998 |
| WO | 02051379 | 7/2002 |
| WO | 03049674 | 6/2003 |

OTHER PUBLICATIONS

Cosmetic Chemistry of Natural Jojoba retrieved from http://www.purcelljojoba.com/JojobaTechInfo/JojobaChemistryGuide/JojobaChemistryGuideEnglish.pdf, on Nov. 21, 2007.
Driver and Lemp, "Meibomian gland dysfunction", Surv Ophthalmol 40:343-367 (1996).
Final Report on the Safety Assessment of Jojoba Oil and Jojoba Wax, J Amer College Toxicology, 11(1):57-74. (1992).
McCulley and Shine, "Meibomian gland function and the tear lipid layer" The Ocular Surface 1(3):97-106 (2003).
Super-Moisturizer retrieved from http://www.royalwomen.com/USA/Cosmetics/jojoba/super moisturizer.hm, on Feb. 24, 2004.

*Primary Examiner* — Qiuwen Mi
(74) *Attorney, Agent, or Firm* — Pabst Patent Group LLP

(57) ABSTRACT

A jojoba formulation has been developed for administration to the meibomian gland, for treatment of the symptoms of dry eye, and/or for drug delivery to the meibomian gland. The formulation incorporates the natural product jojoba wax, or components thereof, to enhance the spreading of the artificial tear as well as stabilize the tear film. The jojoba wax tear relieves irritation and discomfort as well as sharpens the blurred vision. Jojoba, because of its close chemical and physical properties to meibomian gland secretions, is effective upon topical application to penetrate the lid margin to reach the gland tissues where it may exert a therapeutic effect with or without an adjunctive agent.

11 Claims, No Drawings

TREATMENT FOR MEIBOMIAN GLAND DYSFUNCTION OR OBSTRUCTION

CROSS REFERENCE TO RELATED APPLICATIONS

This application is a divisional of U.S. Ser. No. 12/780,730 filed Mar. 1, 2005, entitled "Treatment for Meibomian Gland Dysfunction or Obstruction" by Steven Maskin, which is a continuation in part of U.S. Ser. No. 11/069,239 filed Mar. 1, 2005, now abandoned, which claims priority to and benefit of U.S. Provisional Application Ser. No. 60/552,577 filed Mar. 12, 2004 and U.S. Provisional Application Ser. No. 60/562,683 filed Apr. 15, 2004, all of which are herein incorporated in their entirety by reference.

BACKGROUND OF THE INVENTION

This invention is generally in the field of ocular lubricants, and in particular relates to a formulation for treatment of the symptoms of dry eye.

The surface of the eye requires constant lubrication for proper function. This includes quality of vision as well as comfort. The eye becomes irritated and vision blurs when inadequately lubricated. This condition is frequently referred to as dry eye. Inadequately treated severe dry eye can lead to cornea scarring, blindness and even loss of the eye. Dry eye is a common condition and many over-the-counter and even prescription therapies are available to mitigate this at times difficult and annoying condition. Many patients are unable to find relief with present therapies.

The meibomian gland secretions of the eyelid provide the lipid layer of the tear film. The major component of the meibomian gland lipid secretions are wax esters (Driver and Lemp, Meibomian Gland Dysfunction, Surv Ophthalmol 40:343-367, 1996). The meibomian gland function and therefore quality and quantity of lipid for the tear film is influenced by biologic processes which may lead to a dysfunctional gland with or without obstruction of the meibomian gland outflow ducts. These obstructions include abnormally thick meibum secretions as well as keratinized cellular material and possible fibrovascular tissue as well as gland orifice fibroses, vascularization and keratinization.

Providing effective anesthetic to the meibomian gland tissues is of significant importance to prepare for intraductal surgery to physically unblock the impacted ducts. This surgical probing procedure can be performed in the office with adequate anesthesia. There is a great demand for a topical anesthetic to avoid the pain associated with needles. Topical anesthetics which are liquid fail to provide adequate anesthesia for this procedure as the liquid quickly evaporates.

It is therefore an object of the present invention to provide a formulation for enhancing and alleviating meibomian gland function.

It is a further object of the present invention to provide a formulation for delivering drugs, especially topical or local anesthetics, to the meibomian gland tissues.

SUMMARY OF THE INVENTION

Jojoba formulations have been developed for administration to the meibomian gland, for treatment of the symptoms of dry eye, and/or for drug delivery to the meibomian gland. A jojoba emulsion formulation incorporating jojoba wax, or components thereof, to enhance the spreading of the artificial tear as well as stabilize the tear film, relieving irritation and discomfort as well as sharpening blurred vision, has also been developed. Jojoba, because of its close chemical and physical properties to meibomian gland secretions, is effective upon topical application to penetrate the lid margin to reach the gland tissues where it may exert a therapeutic effect with or without an adjunctive agent.

DETAILED DESCRIPTION OF THE INVENTION

Jojoba formulations have been developed for administration to the meibomian gland, for treatment of the symptoms of dry eye, and/or for drug delivery to the meibomian gland.

In one embodiment, a jojoba emulsion formulation providing comfort and clarity of vision to patients with dry eye has been developed. The wax esters of the jojoba improve and enhance the spreading, stability and lubricating effect of the artificial tear on the tear film.

In a second embodiment, a topical jojoba ointment formulation has been developed to apply to the lid margin to reduce meibomian gland duct obstruction as well as deliver adjunctive therapeutic and anesthetic agents to glandular tissues. Jojoba is comprised of over 97% wax esters of the long chain variety similar to that derived from the meibomian gland destined for the lipid tear film. These lipid intraductal impactions can be liquified for better flow through the use of a jojoba wax containing therapy. The jojoba wax penetrates into the meibomian gland tissues and therefore can be used to deliver or chaperone an adjunctive agent to the meibomian glands or ducts to further liquify existing secretions or modulate meibomian gland function or to deliver a topical anesthetic to the gland tissues.

This formulation overcomes the side effects and problems associated with numerous topical gel anesthetics both presently commercially available as well as specially compounded using non-jojoba containing preparations. Formulations containing higher concentrations of lidocaine, up to 21%, or with tetracaine up to 8%, in a plasticized base as well as a liposome containing base have been used without success in without obtaining adequate anesthesia. The anesthetic itself was very irritating to the patient and had to be irrigated off the eye and lid.

I. Formulation

The formulation to treat meibomian gland dysfunction including orifice or duct obstruction may include jojoba alone (i.e., "neat"), or in a semi-solid formulation with petrolatum ointment. The jojoba may be used to deliver an adjunctive active agent. In this indication, the jojoba is first mixed with the adjunctive agents. For example, to anesthetize the meibomian gland in preparation for intraductal surgical probing, the jojoba is mixed with lidocaine powder to reach the desired concentrations of lidocaine anesthetic. The preparation must be well mixed to avoid lidocaine clumping with inconsistent concentrations of anesthetic in the formulation which could lead to potential toxicity. This jojoba-lidocaine mixture is then further mixed with petrolatum to achieve the final desired concentrations.

For application to the eye as a treatment for dry eye, the formulation is an emulsion of Jojoba wax emulsified in a pharmaceutically acceptable aqueous solution. The emulsion can contain a separate non jojoba emollient, wherein the ratio of the jojoba to the optional additional emollient is from (greater than 1):5 to 500:1. The jojoba wax must be present in a sufficient concentration to form an emulsion—too little or too much, and no emulsion will be formed.

A. Jojoba Wax

The formulation contains jojoba wax in an emulsion. The jojoba wax performs as lubricant and evaporation retardant for the tear film. Jojoba's melting point is about 6° C. It is extracted from seeds and leaves of the jojoba tree (*Simmondsia chinensis*) cultivated in the desert conditions of Arizona and California as well as Northern Mexico and other locations. The chemical structure does not vary with plant type, growing location, soil type, rainfall or altitude. The oil produced by jojoba lacks triglycerides. It does not contain glycerol combined with fatty acids. Rather the jojoba combines fatty alcohols with fatty acids to produce a vegetable oil which is actually a liquid wax, having its own type of molecular size and shape with unusual anti-evaporative properties which protect the shrub from its severe arid natural habitat. Jojoba wax or the wax esters therein keep the shrub well lubricated and moisturized yet it is non occlusive. The non-occlusive property is related to its porosity. In the shrubs and trees it is derived from, the porosity allows for evaporative exchange of vapors thus cooling the jojoba tree in its hot native climate.

Jojoba wax is non toxic and biodegradable and is pasteurized to kill microorganisms (National Research Council. 1985. *Jojoba: New Crop for Arid Lands, New Material for Industry*. National Academy Press, Washington, D.C.). The liquid wax commercially available does not include those solid components of the seed which have toxic effects, the glycosides simmondsin and simmondsin-2-ferulate.

Jojoba wax is a liquid wax composed of long chain wax esters. The natural jojoba is 97% wax esters with few impurities. There are no resins, tars, or alkaloids and only a trace amount of saturated wax, alcohols, fatty acids, and hydrocarbons. The components of the jojoba wax esters include long chain alcohols esterified with long chain fatty acids with a total of 38 to 44 carbon atoms. Exemplary long chain fatty acids include gadoleic, palmitic, palmitoleic, stearic, oleic, linoleic, arachidic, linolenic, eicosenoic, behenic, erucic, lignoceric, lactic, decate, acetic and myristic fatty acids. The fatty acids typically have carbon chains of C12 to C30, with or without various degrees of saturation or unsaturation. The alcohol components of the wax ester contain carbon chains between C16 and C32 with or without various degrees of saturation or unsaturation. The alcohol component may be eicos-11-enol, docos-13-enol, tetracos-15-enol, myristyl alcohol, octyldodecyl stearoyl alcohol or cetyl alcohol.

The wax esters are comprised of alcohols esterified with long chain fatty acids with a total of 38 to 44 carbon atoms. The fatty alcohols are predominantly 20 and 22 carbon atoms with one double bond. Its fatty acids are mostly 20:1 (70%), with some 22:1 (20%) and the remainder 18:1 (10%). All double bonds have a cis configuration and are spaced widely apart equidistant from the ester linkage creating an especially stable molecule resistant to oxidation. The cis double bond configuration is also felt to give the jojoba its porosity.

Jojoba wax is approved by the Food and Drug Administration ("FDA") for use in cosmetics and other formulations for application around the eyes, although not for direct application to the eye. Jojoba wax is used extensively in the cosmetic industry in up to at least a 10% in water emulsion, in eye makeup remover, as well as for skin and hair products. It is also used in therapeutic massage. Primary eye irritation studies have been performed in rabbits using undiluted refined jojoba liquid wax. Slight irritation was noted which resolved within 24 hours. A 20% natural jojoba wax dropped in rabbit eyes was concluded a nonirritant (Final Report on the Safety Assessment of Jojoba Oil and Jojoba Wax, J Amer College Toxicology, 11 (1), 1992, 57-74.) The Environmental Protection Agency (EPA) in the Federal Register 40 CFR Part 180, 1995 acknowledged the wide distribution of Jojoba in commerce and availability to the general public throughout the United States without any evidence of significant adverse effects to humans or the environment. The Cosmetic Ingredient Review lists Jojoba as safe to use.

Jojoba wax has also been shown to help break down sebum in plugged up sebaceous pores of the skin. It may prove to also be able to break down and unplug the modified sebaceous (meibomian) glands of the lid when applied as a drop or an ointment or other topical therapy. Furthermore, adjunctive agents may be added to the ointment such as an anesthetic or therapeutic.

Jojoba wax also has intrinsic antimicrobial properties which include activity against envelope viruses, mold, fungus and bacteria. U.S. Pat. Nos. 4,585,656 and 6,559,182 describe the efficacy of treating envelope viruses with jojoba wax esters. In vitro experiments in the literature showed jojoba has an intense inhibiting effect on Mycobacterium tubercle bacilli. It may be useful as a prophylactic as well as therapeutic agent to prevent and treat ocular or periocular infections. It may be used as therapy for infection of any part of the eye or adnexal structure.

Other jojoba derivatives which may be incorporated into an ophthalmic delivery system include jojoba esters, jojoba alcohols, and the hydrogenated jojoba solid wax. Jojoba esters are the result of an inter-esterification of various ratios of jojoba liquid wax and hydrogenated jojoba solid wax. The physical consistency ranges from liquid to semi-solid paste or creams. Jojoba solid wax is derived from the hydrogenation and complete reduction of the unsaturated wax esters. It is a hard crystalline wax comparable to beeswax with a melting point of 69° C. and can be prepared in a wax in water emulsion. This wax-in-water emulsion emulsifies easily and may also be used in an ophthalmic preparation. Emulsifying agents for the ophthalmic preparation include stearic acid (4%) and triethanolamine (2%). Jojoba alcohols are generated from a sodium reduction of jojoba liquid wax and hydrogenated jojoba solid wax with subsequent additional refinement. Jojobutter-51 is an isomorphous mixture of jojoba liquid wax, partially isomerized jojoba liquid wax and hydrogenated jojoba solid wax (J Amer College Toxicology, 11 (1), 1992). Sulfurization of jojoba results in enhanced lubricant properties which is further enhanced with phosphorus, bromine or chlorine. (Wisniak J The Chemistry and Technology of Jojoba Oil, Am Oil Chemist Society, 1987) and may optimize the lubrication of an ophthalmic tear supplement.

B. Aqueous Solutions or Emulsion

The wax is mixed with an aqueous solution for application to the eye. Typically the aqueous solution is sterile water or hypotonic or isotonic saline and will contain buffer to physiological pH, in the range of about 7-7.5. It may also be cell culture media such as Dulbecco's Media (DMEM). It can also contain a minor amount, such as 1-5%, surfactant/lubricant/demulcent such as polysorbate 80. Ancillary ingredients to establish the desired tonicity with tears may include electrolytes. Preservatives such as sodium bisulfate, ascorbic acid, alpha-tocopherol, benzalkonium chloride, ethylenediaminetetraacetic acid (EDTA) and chlorhexidine can be used as well as chlorbutanol, sodium perborate and stabilized oxychloro complex. Other preservatives include polyquad, polyhexamethyl biguanide, chlorhexidine, propylparabens and methylparabens and others. Other additives may include humectants such as propylene glycol and sorbitol. Representative pH buffers include sodium borate or mono and di-sodium phosphate or other phosphate, carbonate or acetate salts.

The formulation may further include a sterol, hydroxycarotenoid or Vitamin A optionally esterified with fatty acids of various chain lengths between C10 and C30. The formulation may also include polar lipids including glycolipids, sphingolipids and/or phospholipids including phosphatidylinositol, phosphatidylethanolamine, sphingomyelin, phosphatidylglycerol, and diphosphatidylglycerol, Triglycerides may also be included.

Suitable lubricants used with the wax ester in a concentration between 0.01% to 20% include cellulose derivatives. Examples of cellulose derivatives include carboxymethylcellulose sodium 0.2 to 2.5%, hydroxyethyl cellulose 0.2% to 2.5%, hydroxypropyl methylcellulose 0.2% to 2.5%, and methylcellulose 0.2% to 2.5%. Other examples of lubricants include Dextran 70, (0.1%), gelatin, 0.01%, glycerin, 0.2 to 1%, polyethylene glycol 300, 0.2 to 1%, polyethylene glycol 400, 0.2 to 1%, polysorbate 80, 0.2 to 5%, propylene glycol, 0.2 to 5%, polyvinyl alcohol 0.1 to 5%, and povidone 0.1 to 5%. These lubricants can increase viscosity of the artificial tear as a mucomimetic and may be added to the formulation. The formulation can be thought of as a tear replacement therapy. Additional mucomimetics include carbomer and hyaluronic acid.

Additional classes of additives include lubricants, preservatives, stabilizers, wetting agents, emulsifiers, buffers, and different salts to alter osmotic pressure, as well as solubilizing agents, dispersants, and detergents.

The wax can also be added to artificial tears obtained over the counter ("OTC"). Examples include VISINE™ marketed by Pfizer, REFRESH TEARS™ product line marketed by Allergan, SYSTANE™ marketed by Alcon, GENTEAL™ marketed by Novartis, and OCUCOAT™ marketed by Bausch and Lomb.

Ophthalmic astringents may also be included. One example is zinc sulfate, 0.25%. A hypertonicity agent may be used such as sodium chloride 2 to 5%. An ophthalmic vasoconstrictor may be used including ephedrine hydrochloride, 0.123%, naphazoline hydrochloride, 0.01 to 0.03%, phenylephrine hydrochloride, 0.08 to 0.2% and tetrahydrozoline hydrochloride, 0.01 to 0.05%.

Proteins normally found in the tear may be included in the formulation to further increase stability. These may include amongst others, prealbumin, albumin, lyzozyme, lactoferrin, beta lactoglobulin, IgA as well as lipocalins.

Suitable electrolytes include sodium chloride, potassium chloride, sodium phosphate, potassium phosphate, sodium and potassium sulfates and sodium and potassium bicarbonates. Suitable non electrolytes such as glycerin and sugars such as urea, sorbitol, glucose and sucrose can also be added.

C. Emulsion, Lotion or Ointment Formulations

The jojoba wax concentration in an aqueous carrier will typically be between 0.001% to 50%. The jojoba in aqueous emulsion may include a second emollient such as mineral or light mineral oil. Other emollients may be used in the emulsion such as white petrolatum, white ointment, paraffin, and beeswax or other wax. These emollients may be used to increase the viscosity of the emulsion. The ratio of jojoba to the second emollient is from greater than 1:5 to 500:1.

In another embodiment, the jojoba wax, up to 70%, is formulated in an ointment emollient. A suitable carrier includes a mixture of mineral oil and petrolatum in a ratio of about 70% to 30%, paraffin up to 5%, white ointment up to 100%, white petrolatum up to 100%, petrolatum up to 100%, white wax up to 5%, yellow wax up to 5%, colorless jojoba wax up to 50%, lanolin 1 to 10% and anhydrous lanolin 1 to 10%.

D. Active Agents

The formulation can also be used as a platform to deliver active agents. Active ingredients that can be used include anesthetics, anti-glaucoma therapies, antibiotics, antimicrobial peptides, antivirals, antiparasitics, antifungals, antiinflammatories, antihistamines, anti-allergy therapies, hormones such as androgens and others, vitamins, growth factors, cytokines, mucins, surface stimulating drugs, immunomodulators, immune response modifiers, cytokine modifying agents, immunosuppressive agents, antineoplastic agents, eyelash growth stimulators and other medicaments including keratolytic agents.

II. Methods of Use

In the preferred embodiment for treatment of dry eye, the formulation is administered once to four times a day directly to the eyes of the individual in need thereof. The frequency will vary depending on the severity of symptoms. The formulation may be applied as a drop in the form of an emulsion or suspension, liposome, lotion, ointment, cream, gel, salve or powder and sustained or slow release, as well as eyelid lotion. It may also be used as an eye wash or rinse to irrigate the eye. The formulation may also be applied in a sprayable form. This lubricant will be extremely helpful in eradicating the symptoms of dry eye in the various settings it occurs. This includes the most common settings of age related so called dry eye syndrome, computer related dry eye, dry eye after Lasik, and dry eye associated with reading, driving or watching a movie or television. Patients with contact lens intolerance or who use an ocular prosthesis will also greatly benefit from the enhanced lubrication. Other examples include patients with a history of eye surgery and dry eye. This includes cataract surgery, cornea surgery and cornea transplants. Patients with neurologic disorders such as Bell's Palsy or other neuroparalytic as well as neurotrophic disease will also benefit. Lagophthalmous characterized by an exposed ocular surface which can occur while sleeping or even during waking hours will be improved with the ointment, and/or gel form of this lubricant. Devastating although rare mucous membrane blistering diseases as Stevens Johnson Syndrome are also associated with both a watery and lipid dry eye due to fibrotic changes associated with glandular tissues. The jojoba formulation should be especially helpful to replace lipid and aqueous deficiencies and help relieve suffering to comfort an otherwise extremely painful eye.

Other types of dry eye characterized by plugged, inflamed and/or dysfunctional sebaceous glands of the lid known as meibomian gland dysfunction should also be improved with use of this formulation applied to the eyelids. One example is in the setting of preparation for intraductal meibomian gland probing where a topical jojoba is used to increase penetration of an anesthetic, thereby enabling a well anesthetized meibomian gland leading to a well tolerated office procedure obviating needle injection or moving the patient to an operating g room. All other commercially available anesthetics suitable for ophthalmic use were evaluated and found inconsistent in effectiveness. Many patients reported discomfort and some patients had to limit the extent of probing because of lid sensitivity. This would then require a more lengthy additional application of anesthetic which helped in limited cases. Using a jojoba lidocaine anesthetic ointment has successfully enabled patients suffering from meibomian gland disease and intolerant of other anesthetics to obtain satisfactory levels of anesthesia, allowing the probing procedure to proceed.

The presently preferred embodiment is Lidocaine 8% and Jojoba 25% in a petrolatum ointment base. The lidocaine may range from 2% to 20% while the jojoba concentration may range from 5% to 50%, of the formulation.

Patients with eye infections of the lid, conjunctiva, cornea and tear apparatus and lacrimal gland should also benefit with application of this formulation in one or more forms to the eyelids, conjunctiva, and cornea as well as tear film and other adnexal structures including lacrimal gland, and tear outflow system including puncta, canaliculi, and lacrimal sac.

In preliminary studies on skin, Jojoba wax has been shown to relieve pain and reduce swelling from superficial thermal and chemical burns. There may also be a therapeutic effect on ocular burns.

The formulation can also be used to prevent, treat or alleviate the symptoms of envelope viruses including herpes simplex keratitis, and varicella zoster keratitis which causes chicken pox and shingles. Other viral infections of the eye that may be treated include human herpes virus 8 (HSV 8), Kaposi sarcoma as well as Epstein-Barr virus, cytomegalic inclusion virus (CMV) and Human Immunodeficiency Virus (HIV).

Non-ocular uses of the formulation include use to treat or prevent accumulation of ear canal wax, treatment of vaginal dryness or other symptoms of perimenopausal dryness, moisturizing dry nasal mucosa or where the patient has a sinus condition, including inflammation or infection.

The present invention will be further understood by reference to the following non-limiting examples.

Examples

Example 1

Jojoba Formulations for Treatment of Dry Eye

The surface of the eye requires constant lubrication for proper function, and inadequate lubrication results in irritation and blurred vision, a condition frequently referred to as dry eye. Dry eye is a common condition and many over-the-counter and prescription therapies are available to patients. However, many patients are unable to find relief with present therapies. Jojoba neat was applied to the eye and was found to be extraordinarily comfortable with eye closure. Once the eye was opened it would feel heavy and uncomfortable. To optimize its potential, I decided to emulsify the jojoba in an aqueous solution whereby the unique properties of jojoba could be used to comfort the patient while the eye was opened or closed.

Patients were treated with Ophthalmic Lubricant containing different concentrations of wax using the claimed method as shown in the Exhibits.

In a preferred embodiment, the formulation contains 0.5-5% jojoba wax, most preferably 0.5 to 2% jojoba, 1% polysorbate 80 in a aqueous buffered saline based liquid wax emulsion.

The 2% jojoba formulation was administered to a total of 16 volunteer individuals with different types of irritated eyes. The drop was reported to be extremely comfortable for all individuals without causing visual blur.

Three volunteers had painful dry eye after Lasik. None of the conventional therapies had helped them thus far. For PC, AS, and KA, relief was immediate and lasted about 8-10 hours.

For TB who said his irritation was allergic in nature, none of the presently available OTC drops had helped relieve his severe symptoms. One drop of the jojoba wax formulation applied to each eye relieved all symptoms for the entire day.

For JR who said his eyes are always irritated in the morning, get red and stay red for hours and who has yet to find a comfortable and effective OTC eyedrop, one drop of the jojoba wax formulation applied to each eye eliminated the red eyes and comforted his eyes for the entire day.

Two individuals (RD and AM) used the jojoba wax formulation in the setting of soft contact lens wear and found its comforting properties to be truly unique. They enjoyed instant relief of eye discomfort which lasted the entire day.

One individual (ST) used the jojoba wax formulation in the setting of rigid contact lens wear and also had instant relief of eye irritation lasting the whole day.

In summary, the volunteers were extremely pleased by the comfort, immediate and lasting relief of the jojoba wax formulation.

Three additional patients (HK, LF, and IM) with cornea erosions were placed on this formulation using 1% jojoba wax. The drop was used four times per day. The drop was well tolerated, and was found to be soothing and very comfortable. Within one to two weeks the erosions were markedly and almost completely resolved.

A formulation consisting of 5% jojoba in aqueous with additional 0.05% white petrolatum USP was created using a heating stir plate and was placed in the right eye of 6 volunteers. For MB, MH, DN, HL, AM, and SM the drop was well tolerated, comfortable and felt thicker than 5% jojoba in aqueous emulsion without the petrolatum.

The formulation was also evaluated on two volunteers using lipid tear interferometry. A drop of the formulation was placed in one eye and an artificial aqueous tear in the other. The interferometry pattern showed thick blue waves of liquid wax quickly mixing with the volunteer's own lipid tear within seconds. The resultant lipid tear pattern showed a healthy enhanced film at least three hours later. Breakup times were also prolonged therapeutically in the eye receiving the emulsion compared to the fellow eye.

In Summary:

A patient with dry eye problems in the right eye and who had previously been unable to find relief with the use of Visine®, was administered one drop of Ophthalmic Lubricant ½% to both eyes, once a day.

A patient who presented with decreased vision in the right eye and dry eyes, and who had been unable to find relief with the use of Natural® tears, Refresh Plus®, Refresh® tears, and Bion® tears, was administered Ophthalmic Lubricant 5% four times a day.

A patient who presented with dry eyes with resultant severe burning, itching, and nerve pain, and who had been unable to find relief with the use of Restasis®, Refresh® Liquigels, Refresh® contacts, Visine® for contacts, and Lotomax®, was administered ophthalmic lubricant 2% four times a day.

A patient who presented with dry eyes due to Lasik surgery, and who had been unable to find relief with the use of Genteel®, Refresh Endure®, Refresh Plus®, Refresh PM®, Refresh® tears, Restasis®, Thera Tears®, and Soothe and Sustain®, was administered Ophthalmic Lubricant 2% to both eyes four to six times a day.

A patient who presented with chronic burning pain and dry sensation in the eyes, blurry vision, and sensitivity to light, and had previously used Hypo Tears®, Natural Tears®, Refresh® Liquigels, Refresh Plus®, Refresh Tears®, Refresh® PM, Visine®, Bion® Tears, and Systane® without any relief. Ophthalmic Lubricant 2%, was administered four times a day.

A patient who presented with decreased vision due to a history of herpes zoster ophthalmicus of the right eye, and dry eye, and who had been unable to find relief with the use of Genteel®, Natural Tears®, Refresh Liquigel®, Refresh Plus®, Refresh Tears®, Refresh PM®, and Systane®, was administered Ophthalmic Lubricant 2% to the right eye four times a day.

A patient who presented with severe dry eyes with light sensitivity, foreign body sensation, and Sjorgren syndrome, and who had been unable to find relief with the use of Genteel®, Refresh Endure®, Hypo Tears®, Refresh Liquigel®, Refresh Plus®, Refresh Tears®, Restasis®, Visine®, and Systane® was administered Ophthalmic Lubricant 2% to both eyes four times a day.

A patient who presented with severe dry eye, pain, inflammation and light sensitivity of the left eye, and who had been unable to find relief with the use of Genteel®, Thera Tears®, and Lacrilube®, was administered Ophthalmic Lubricant 15% four times a day to both eyes.

All of the patients treated obtained relief for the conditions treated and testified to obtaining better relief with the Ophthalmic Lubricant composition used, when compared to over compositions previously used.

Example 2

Treatment of Meibomian Glands

One drop of routinely available topical anesthetic such as tetracaine 0.5% or proparacaine is applied to the conjunctival sac in each eye for direct treatment to the meibomian glands for intraductal probing. Lidocaine 8% with Jojoba 25% in the petrolatum ointment base is then applied to the lid margin. The patient closes the lids for 15 minutes and is then ready for the lid procedure to probe the meibomian glands after one additional drop of tetracaine or proparacaine.

Studies conducted on twelve patients, 48 lids prepared for probing with the jojoba anesthetic ointment, have been successfully anesthetized for intraductal probing.

The lid margin is where the openings or orifices of the meibomian glands are located. The jojoba, being of wax esters, is able to penetrate effectively and rapidly into the meibomian gland tissues whose main secretion are also wax esters, chaperoning the topical anesthetic. Therefore, the jojoba helps not only to unblock obstructed meibomian glands in various disease states by liquefying abnormal intraductal secretions but also acts as escort or chaperone for additional drug delivery into the glandular tissue.

Modifications and variations of the present invention will be obvious to those skilled in the art from the foregoing detailed description and are intended to come within the scope of the following claims. All references herein are expressly incorporated by reference.

I claim:

1. A method of treating obstructed or dysfunctional meibomian glands comprising applying an effective amount of a jojoba wax formulation to penetrate the lid margin and reduce meibomian gland obstruction.

2. The method of claim 1 comprising applying an ointment comprising an effective amount of jojoba wax or derivative thereof, or a component thereof.

3. The method of claim 2 wherein the component is a wax ester and/or alcohol esterified with long chain fatty acids with a total of 12 to 62 carbon atoms.

4. The method of claim 1 comprising a jojoba concentration from 5% to 50% by weight of the formulation.

5. The method of claim 1 comprising applying a semi-solid ointment or cream, wherein the ointment or cream base is a semi-solid selected from the group consisting of a mixture of mineral oil and petrolatum in a ratio of about 70% to 30%, paraffin up to 5% by weight of the ointment or cream base, white ointment up to 100% of the ointment or cream base, white petrolatum up to 100% by weight of the ointment or cream base, petrolatum up to 100% by weight of the ointment or cream base, white wax up to 5% of the ointment or cream base, yellow wax up to 5% by weight of the ointment or cream base, mineral oil up to 50% by weight of the ointment or cream base, light mineral oil up to 50% by weight of the ointment or cream base, lanolin 1 to 10% by weight of the ointment or cream base, and anhydrous lanolin 1 to 10% by weight of the ointment or cream base.

6. The method of claim 1 wherein the formulation comprises a local anesthetic.

7. The method of claim 6 wherein the formulation comprises from 2 to 20% Lidocaine by weight of the formulation.

8. The method of claim 2 wherein the formulation comprises 8% lidocaine and 25% Jojoba by weight of the ointment in a petrolatum ointment base.

9. The method of claim 1 comprising administering the formulation to the lid margin to unblock the modified sebaceous glands of the eyelid known as meibomian glands.

10. The method of claim 1 to provide relief wherein the patient has meibomian gland dysfunction.

11. The method of claim 1, wherein the effective amount of a jojoba wax formulation comprises a combination of jojoba wax and jojoba wax ester and/or alcohol esterified with long chain fatty acids with a total of 12 to 62 carbon atoms.

\* \* \* \* \*